United States Patent [19]

Colpitts et al.

[11] 4,281,992

[45] Aug. 4, 1981

[54] PROSTHETIC DENTURE PREPARED FROM POLYURETHANE ELASTOMER

[75] Inventors: Ralph W. Colpitts, Chesterfield; Jens H. Wendt, Springfield, both of Mo.

[73] Assignee: Polythetics, Inc., St. Louis, Mo.

[21] Appl. No.: 96,680

[22] Filed: Nov. 23, 1979

Related U.S. Application Data

[62] Division of Ser. No. 13,159, Dec. 21, 1979, Pat. No. 4,225,696.

[51] Int. Cl.$^3$ .............................................. A61C 13/00
[52] U.S. Cl. .................................... 433/212; 433/199; 433/201; 433/202; 528/66; 528/76; 106/35
[58] Field of Search ................ 433/199, 201, 202, 212

[56] References Cited

U.S. PATENT DOCUMENTS

| | | | |
|---|---|---|---|
| 4,024,636 | 5/1977 | Colpitts et al. | 433/199 |
| 4,024,637 | 5/1977 | Colpitts et al. | 433/199 |
| 4,080,412 | 3/1978 | Colpitts et al. | 264/17 |
| 4,110,184 | 8/1978 | Dart et al. | 528/80 |

*Primary Examiner*—Harold D. Anderson
*Attorney, Agent, or Firm*—Scully, Scott, Murphy & Presser

[57] ABSTRACT

A hard, substantially non-hydrophilic polyurethane elastomer denture is disclosed in which the elastomer possesses a hardness of not less than about Shore D60 and preferably not greater than about Shore D100. The polyurethane elastomer is prepared from a polyether polyol and an aromatic polyisocyanate in which the isocyanate groups are bonded directly to the aromatic nucleus. The aforesaid hard non-hydrophilic polyurethane elastomer can constitute the entire material of which the denture is made, including the teeth if so desired, or it can be employed as the tooth-holding portion of the denture in combination with a soft, substantially non-hydrophilic elastomer as the mouth-engaging portion of the denture. The hard non-hydrophilic polyurethane elastomer possesses superior resistance to thermal distortion under the conditions prevailing in the mouth.

11 Claims, No Drawings

PROSTHETIC DENTURE PREPARED FROM POLYURETHANE ELASTOMER

This is a division, of application Ser. No. 013,159, filed Dec. 21, 1979 now U.S. Pat. No. 4,225,696.

BACKGROUND OF THE INVENTION

1. Field of the Invention

This invention relates to the field of artificial dentures, and more particularly, to such dentures prepared from polyurethane elastomers.

2. Description of the Prior Art

It has been proposed to provide dentures with a soft layer in contact with the gums and other mouth parts to provide tissue relief. Such soft layers have been composed of acrylics, silicones, and like rubber-like materials. But on aging, such soft layers tend to harden and give off undesirable odors. In addition, some decomposition of the polymer may also occur presumably due to an oxidation process as well as to pH fluctuations within the mouth. By way of overcoming these disadvantages, U.S. Pat. No. 4,024,636 and 4,080,412, both to Colpitts et al., and both incorporated by reference herein, describe dentures in which teeth are anchored in a gum member comprising a tooth-holding portion fabricated from a hard non-hydrophilic polyurethane elastomer having a hardness of not less than about Shore D40, and a mouth-engaging portion fabricated from a soft non-hydrophilic polyurethane elastomer having a hardness of not greater than Shore A65 integrally and chemically bonded into a unitary mass. U.S. Pat. No. 4,024,637 to Colpitts which is also incorporated by reference herein describes a denture in which hard non-hydrophilic polyurethane elastomer teeth are imbedded in and chemically bonded to a soft non-hydrophilic polyurethane elastomer. Preferred non-hydrophilic elastomers are those formed by isocyanate-terminated prepolymers which are cross-linked or cured by mixing with a cross-linking agent and heating as required to effect curing. Isocyanate-terminated prepolymers suitable for preparing the hard non-hydrophilic polyurethane elastomers are prepared by the reaction of polyether diols or triols with aliphatic or cycloaliphatic or aralkyl di- or polyisocyanates in proportion to give free NCO groups. The prepolymers are then cured or cross-linked with a diol, polyol, an alkanolamine, a diamine or a tertiary amine containing polyol, or blends thereof. Advantageously, the diol or polyol is a polyether diol or polyol or a hydroxyl-terminated prepolymer. While dentures prepared from the foregoing polyurethane resins represent a significant advance over dentures fabricated from such materials as acrylic resins, silicones, and the like, it has been observed that the polyurethanes are susceptible to distortion under the conditions prevailing in the mouth. Such distortion, accompanied by a loss in dimensional stability of the dentures, interferes with the ability of the dentures to retain a good fit with the mouth and remain in place without slippage.

SUMMARY OF THE INVENTION

It has now been discovered that polyurethane elastomers for use in artificial dentures can be provided with enhanced resistance to thermal distortion under the conditions of use when prepared from a polyether polyol and an aromatic polyisocyanate in which the isocyanate groups are bonded directly to the aromatic nucleus and not to an aliphatic group as in the polyisocyanates employed in the preparation of known polyurethane elastomer dentures. As a result of the excellent degree of resistance to thermal distortion, dentures made with the aromatic polyisocyanate-based hard polyurethane elastomers herein retain a close fit with the mouth and are virtually free of any tendency toward slippage to which dentures made with prior polyurethane resins are liable.

Thus, in accordance with the present invention, a prosthetic denture is provided which is fabricated with a hard, substantially non-hydrophilic polyurethane elastomer with a hardness of not less than about Shore D60 and preferably not greater than about Shore D100, the elastomer being prepared from the reaction of a polyether polyol and an aromatic polyisocyanate in which the isocyanate groups are bonded directly to the aromatic nucleus.

While the hard polyurethane elastomer can be used in the preparation of the entire denture, including the teeth if so desired, it is also within the scope of this invention to utilize the hard polyurethane elastomer as the tooth-engaging portion of the denture bonded to a soft, substantially non-hydrophilic elastomer employed as the mouth engaging portion of the denture. The latter elastomer can be selected from among any of the soft resins heretofore known and/or used in dental prostheses including the soft non-hydrophilic polyurethane elastomers of U.S. Pat. Nos. 4,024,636 and 4,080,412 to Colpitts et al., supra, which have a hardness of not greater than about Shore A65 and preferably not less than about Shore A15. Advantageously, the soft resin is a polyurethane prepared with a polyether polyol and an aromatic polyisocyanate in which the isocyanate groups are bonded directly to the aromatic nucleus. Accordingly, the invention herein further comprises a denture in which hard polyurethane elastomer and soft polyurethane elastomer elements as aforedescribed are bonded to form a unitary whole.

DESCRIPTION OF THE PREFERRED EMBODIMENTS

The polyether polyols which can be used herein can be selected from amongst any of the polyether polyols heretofore employed in the preparation of polyurethanes. Such polyols possess two, and preferably, three or more hydroxyl groups. Among the useful polyether polyols are included the poly-(oxypropylene) glycols, the poly-(oxypropylene)poly-(oxyethylene) glycols, the poly-(1,4-oxypropylene) glycols and graft copolymers of the poly-(oxypropylene)-(polyoxyethylene) glycols with acrylonitrile or mixtures of acrylonitrile and styrene. The equivalent weight of these polyether diols can range between 200 to 1000 with a preferred range of 200 to 400. The polyol may consist of simple polyfunctional alcohols such as glycerine, trimethylolpropane, 1,2,6-hexanetriol, or pentaerythritol, or they may consist of polyether triols such as poly(oxypropylene) or poly(oxyethylene) adducts of the above polyols. The equivalent weight of the polyether polyols may range between 100 to 800 with a preferred range of 100 to 500. It is also understood that various combinations of diols and polyols may be used.

The aromatic polyisocyanates used for the preparation of the hard polyurethane elastomers and optional soft polyurethane prepolymers must contain the isocyanate groups directly bonded to the aromatic nucleus. Such aromatic isocyanates include, but are not limited to, 2,4-tolylene diisocyanate (TDI), isomeric mixtures of TDI, 3,3'-tolidene 4,4'-diisocyanate (TODI), 3,3'-dimethyldiphenylmethane 4,4'-diisocyanate, diphenylmethane, 4,4'-diisocyanate (MDI), mixtures of MDI and adducts of MDI, etc. The elastomers can be prepared by either the prepolymer method in which a prepolymer having a ratio of NCO to OH groups greater than 1:1 is prepared in a first step followed by chain extension and cross-linking of the prepolymer to form the finished elastomer, or by the one-shot method in which all of the reactants are mixed in a single step to form the final polymer. Both methods are well known in the art (see, for example, *Polyurethanes, Chemistry and Technology*, Part II. Technology by Saunders et al., Interscience 1964).

Aromatic isocyanate-terminated prepolymers suitable for preparing the optional soft polyurethane elastomers (soft prepolymers) are based on polyether diols alone or combinations of polyether diols or triols, and aromatic polyisocyanates. The same diols and polyols as described above may be used but the average equivalent weight is significantly higher than that used in the preparation of the hard polymer. The preferred range of equivalent weight of the polyethers (diols or combination of diols and triols) is 450 to 1500. They are cured in the same way as the hard prepolymers.

The ratio of NCO to OH in the preparation of the optional soft isocyanate-terminated prepolymer may range between about 1.75 to about 2.5 with a preferred range of about 2.0 to about 2.25, while the NCO/OH of the hard isocyanate-terminated prepolymers should have a free NCO content of about 3.5 to about 5.5 percent, preferably about 3.7 to about 4.7 percent, and the hard isocyanate-terminated prepolymers, a free NCO content of about 9.5 to about 14 percent, preferably about 10 to about 13 percent.

For the curing (cross-linking) of the hard and soft prepolymers, preferred polyols are tertiary amine-containing polyols such as poly(oxypropylene) or poly(oxyethylene) adducts of diamines or triamines, such as ethylenediamine, diethylene triamine, polyenediamine, phenylenediamine, or aniline, or any diols, polyols or their blends. Advantageously, they are polyols of relatively low molecular weight such as are obtained by condensing propylene oxide with ethylenediamine or pentaerythritol to a molecular weight of about 500, or of trimethylolpropane or any other base compound to a molecular weight up to 2500.

Another preferred curing or cross-linking agent is a hydroxyl-terminated prepolymer. These are prepared essentially the same way as the aromatic isocyanate-terminated prepolymers but the ratio is such that there are free and unreacted hydroxyl groups. The same diols and polyol and aromatic isocyanates can be used, though it is preferred that the prepolymer have a functionality greater than about 2, which can be obtained by using a polyol having a functionality greater than about 2 and/or an aromatic isocyanate having a functionality greater than 2.

The ratio of OH/NCO in the hydroxyl-terminated prepolymers, advantageously, may be in the same range as the NCO/OH ratio in the aromatic isocyanate-terminated prepolymers. It will be understood, however, that inasmuch as the crosslinking agent may consist of one or more diols or polyols (no isocyanate), the ultimate OH/NCO ratio is infinity.

Another preferred curing or cross-linking agent is a prepolymer-polyol blend. Thus, a polyurethane prepolymer, advantageously, one having neither free NCO nor free OH groups, can be mixed with a polyol, advantageously a polyol having a functionality of more than 2, to form a prepolymer-polyol blend. When such a blend is mixed with an aromatic isocyanate-terminated prepolymer in a NCO/OH ratio of greater than about 1, cross-linking is effected both through an NCO—OH reaction and through NCO-urethane reaction.

When a soft elastomer is joined to a hard elastomer to form a unitary whole, the aromatic isocyanate-terminated prepolymers and the cross-linking agent can be mixed in proportions to give an NCO/OH ratio of at least about 1.05 to about 1.0 and preferably not greater than about 1.1 to about 1.0. This excess of NCO groups ensures a cross-linked polymer which is non-hydrophilic and one which is sufficiently reactive so that the hard non-hydrophilic polyurethane elastomers react chemically with the optional soft non-hydrophilic polyurethane elastomers to form an integral chemical bond between the two. Alternatively, the surface of the hard tooth-engaging elastomer element can be coated with a primer formulation prepared by mixing polyisocyanate with polyol and thereafter applying the soft mouth-engaging elastomer formulation to the surface thus coated. Upon curing of the soft elastomer formulation, a denture will be provided in which the hard and soft elements are permanently bonded to each other.

In order to accelerate the formation of the prepolymers or the cure of both the hard and soft aromatic isocyanate-terminated prepolymers with the cross-linking agents, metal catalysts such as tin catalysts, for example, dibutyltin dilaurate and stannous octanoate, can be used.

In the following resin formulations (all parts by weight) which are illustrative of the invention herein, the ingredients whose properties are given in the Table below were employed.

TABLE

Components of Hard and Soft Non-Hydrophilic Polyurethane Elastomers

| Polyether Polyol Component | Average Molecular Wt. | Hydroxyl No. | Description |
|---|---|---|---|
| Pep 650 (BASF-Wyandotte) | 600 | 376 | Pentaerythritol oxyalkylated with propylene oxide. |
| Pep 450 (BASF-Wyandotte) | 400 | 560 | Pentaerythritol oxyalkylated with propylene oxide. |
| 1,4-butane diol | 90 | 1247 | |
| Polyol 1370 (Wencol, Inc.) | 5600 | 30 | Glycerol oxyalkylated with a mixture of ethylene oxide and propylene oxide. |
| Polyol 1620 (Wencol, Inc.) | 100 | 1160 | Glycerol oxyalkylated with a mixture of ethylene oxide and propylene oxide. |
| Polyol 41–42 | 700 | 232 | Glycerol oxyalkylated with propylene oxide. |
| Polyol 11–27 | 6200 | 27 | Propylene glycol oxyalkylated with ethylene oxide. |

| Aromatic Poly-Isocyanate Component | Description |
|---|---|
| Isonate (Upjohn) Index No. 181 | Mixture of 60% diphenyl methane 4,4'-diisocyanate and 40% higher molecular weight adducts. |
| Isonate (Upjohn) Index No. 143 L | Mixture of diphenyl methane 4,4'-diisocyanate and trifunctional adduct of diphenyl methane 4,4'-diisocyanate. |

Other

TABLE-continued
Components of Hard and Soft Non-Hydrophilic Polyurethane Elastomers

| Component | Description |
| --- | --- |
| Modaflow (Monsanto) 6,000 average molecular weight | Acrylate polymer used as a surface tension modifier |

HARD POLYURETHANE ELASTOMERS
Formulation I
POLYOL COMPONENT

| | |
| --- | --- |
| Pep 450 | 67.75 |
| Polyol 41–42 | 32.25 |
| Modaflow | q.s.* |

AROMATIC ISOCYANATE

| | |
| --- | --- |
| Isocyanate 181 | Indexed at 1.05 |

Formulation II
POLYOL COMPONENT

| | |
| --- | --- |
| Pep 650 | 100 |
| Modaflow | q.s. |

AROMATIC ISOCYANATE

| | |
| --- | --- |
| Isocyanate 181 | Indexed at 1.05 |

Formulation III
POLYOL COMPONENT

| | |
| --- | --- |
| Pep 450 | 100 |
| Modaflow | q.s. |

AROMATIC ISOCYANATE

| | |
| --- | --- |
| Isocyanate 181 | Indexed at 1.05 |

Formulation IV
POLYOL COMPONENT

| | |
| --- | --- |
| Pep 650 | 85 |
| 1,4-butanediol | 10 |
| Polyol 41–42 | 5 |
| Modaflow | q.s. |

AROMATIC ISOCYANATE

| | |
| --- | --- |
| Isocyanate 181 | Indexed at 1.05 |

SOFT POLYURETHANE ELASTOMER
Formulation V
POLYOL COMPONENT

| | |
| --- | --- |
| Polyol 1370 | 98.5 |
| Polyol 1620 | 1.5 |
| Modaflow | q.s. |

AROMATIC ISOCYANATE

| | |
| --- | --- |
| Isocyanate 181 | Indexed at 1.1 |

POLYURETHANE INVESTMENT FORMULATION
Formulation VI
POLYOL COMPONENT

| | |
| --- | --- |
| Polyol 1127 | 82.3 |
| Pep 650 | 17.7 |
| Modaflow | q.s. |

AROMATIC ISOCYANATE

| | |
| --- | --- |
| Isocyanate 143L | Indexed at 1.1 |

*q.s. = quantity sufficient

Comparison was made between two lower dentures (horseshoe-shaped) for resistance to thermal distortion. The dentures were prepared in the same way with the exception that one denture was prepared with a non-aromatic isocyanate (i.e., 4,4'-dicyclohexylmethane diisocyanate, as in the process of the prior art (Denture A) and the other denture was prepared with Isocyanate 181, a mixture of aromatic isocyanates containing 60% diphenyl methane 4,4'-diisocyanate and 40% higher molecular weight adducts, in accordance with the invention herein (Denture B). The cured dentures were each placed in a water bath maintained at a constant 90° F. for a period of 7 days. The dentures were then subjected to approximately equal amounts of flexural force. Denture A which was prepared with the non-aromatic isocyanate readily flexed to a substantial extent under these conditions while Denture B which was prepared with the aromatic isocyanate material remained substantially rigid. Both dentures were then placed in an oven maintained at a constant 195° F. for two hours and then subjected to flexural force. While Denture A exhibited extreme flexibility, Denture B retained its original shape with no appreciable distortion.

MANUFACTURE OF DENTURES

The description whereby dentures are manufactured in accordance with this invention covers three basic situations. In Situation A, a hard denture which can be fabricated of hard polyurethane in accordance with this invention or any polymer heretofore used in the making of dentures is supplied by a dental laboratory or dentist to be provided with a soft polyurethane elastomer liner as described herein. In Situation B, a wax-up denture is supplied by a dental laboratory or dentist to be made into a denture containing both a hard tooth-engaging polyurethane elastomer element and a soft mouth-engaging polyurethane elastomer element. In situation C, the wax-up denture is made into a denture containing hard elastomer only.

I. Situations A, B and C

Upon receipt of the hard denture or wax-up denture as the case may be, the plaster model is sealed (i.e., a coating is placed on all exposed plaster surfaces except the bottom). The denture is then placed in a flask such that the lowest portion of the denture is even with the flask. Investment material is then introduced into the flask until even with the top of the flask. After the investment has set-up, a mold release agent is applied.

II. Situation A (Hard Denture Relined With Soft Elastomer)

The mold release agent is applied to all surfaces, i.e., investment, denture and teeth.

III. Situations B and C (Wax-Up To Be Fabricated Into A Denture)

The mold release agent is supplied to the investment material and a primer, e.g., a solution of isopropyl alcohol and organosilane coupling agent, is applied to the teeth to provide adhesion to the investment.

IV. Situations A, B and C

After the primer or mold release agent has dried (approximately five minutes), additional investment material is applied to cover the entire denture. The flask is then completely sealed by fastening a lid thereon.

V. Situation A

The flask is separated and the denture removed. The denture is then ground out to provide room for the soft polyurethane elastomer.

VI. Situations B and C

The flask is heated in an oven or a hot water bath to melt the wax. The flask is then separated and hot water is forced into the plaster model and mold cavity to remove all traces of excess wax.

VII. Situations A, B and C

Sealer is again applied to all newly exposed plaster surfaces.

VIII. Situation B (Denture Having Hard And Soft Elastomer Elements)

All undercuts are blocked out with duct sealant to facilitate the future removal of the denture without destroying the model.

IX. Situation B and C

Mold release agent is applied to the plaster model and the mold cavity. The liquid hard polyurethane formulation (one-shot) is introduced into the mold cavity and low spots on the plaster model. The plaster model, acting as a lid, is placed on top of the mold, the entire assembly is placed in a clamp and the clamped mold is placed in an oven heated to 85° C. After about five minutes, the assembly is removed from the oven and cooled until comfortable to the touch. The mold is opened and the denture is removed from the investment and plaster model.

X. Situation C (Denture From All Hard Elastomer)

The denture is trimmed, polished, etc., to provide the finished product.

XI. Situation B

The denture is ground out to provide room for the application of the soft polyurethane formulation.

XII. Situations A and B

Following the grinding out of the denture, the denture is coated with anhydrous isopropanol or ethanol and air-dried. A primer (e.g., 7.8 g Pep 650 mixed with 10.0 g Isonate 181) is applied to all surfaces of the denture where the soft elastomer is to adhere. The block-out material is removed from the appropos plaster model. Mold release is again applied to the mold and plaster model and permitted to air-dry (approximately five minutes). The primed denture is then inserted in the mold cavity. Liquid soft polyurethane formulation is introduced into the mold cavity and low spots on the plaster model. Steps IX and X are carried out to complete the manufacture of the denture.

The dentures herein can also be prepared employing any of the other known and conventional techniques known in the art.

What is claimed is:

1. An artificial denture comprising (1) a tooth holding portion integrally applied to (2) a mouth engaging portion, the tooth holding portion prepared from a hard, substantially non-hydrophilic polyurethane elastomer having a hardness of not less than about Shore D60, said hard elastomer consisting essentially of the reaction product of a polyether polyol and an aromatic polyisocyanate in which the isocyanate groups are bonded directly to the aromatic nucleus, the mouth engaging portion comprising a soft, substantially non-hydrophilic elastomer.

2. The artificial denture of claim 1 wherein the soft substantially non-hydrophilic polyurethane elastomer comprising the mouth engaging portion has a hardness of not greater than about Shore A65 and not less than about Shore A15 and consists essentially of the reaction product of a polyether polyol and an aromatic polyisocyanate in which the isocyanate groups are bonded directly to the aromatic nucleus.

3. The artificial denture of claim 1 in which the hard, substantially non-hydrophilic polyurethane elastomer comprising the tooth holding portion is prepared with a polyether diol, triol or tetrol having an equivalent weight of 100 to 800.

4. The artificial denture of claim 3 in which the polyol is derived from pentaerythritol or glycerol oxyalkylated with ethylene oxide, propylene oxide or a mixture thereof.

5. The artificial denture of claim 1 in which the hard, substantially non-hydrophilic polyurethane elastomer comprising the tooth holding portion is prepared from 2,4-tolylene diisocyanate, 2,6-tolylene diisocyanate, 3,3'-tolidene 4,4-diisocyanate, diphenylmethane 4,4'-diisocyanate or mixtures thereof.

6. The artificial denture of claim 1 in which the hard, substantially non-hydrophilic polyurethane elastomer comprising the tooth holding portion has a hardness not greater than about Shore D100.

7. The artificial denture of claim 1 in which the soft, substantially non-hydrophilic polyurethane elastomer comprising the mouth engaging portion is prepared from a polyether diol, triol or tetrol having an equivalent weight of 450 to 1500.

8. The artificial denture of claim 1 in which the soft, substantially non-hydrophilic polyurethane elastomer comprising the mouth engaging portion is prepared from 2,4-tolylene diisocyanate, 2,6-tolylene diisocyanate, 3,3'-tolidene 4,4-diisocyanate, diphenylmethane, 4,4'-diisocyanate or mixtures thereof.

9. An artificial denture comprising (1) a tooth holding portion and (2) a mouth engaging portion, the tooth holding portion comprising a hard polymeric material, the mouth engaging portion comprising a soft, substantially nonhydrophilic polyurethane elastomer having a hardness of not greater than about Shore A65 and not less than about Shore A15, said soft elastomer consisting essentially of the reaction product of a polyether polyol and an aromatic polyisocyanate in which the isocyanate groups are bonded directly to the aromatic nucleus.

10. The artificial denture of claim 9 in which the soft, substantially non-hydrophilic polyurethane elastomer comprising the mouth engaging portion is prepared from a polyether diol, triol or tetrol having an equivalent weight of 450 to 1500.

11. The artificial denture of claim 9 in which the soft, substantially non-hydrophilic polyurethane elastomer comprising the mouth engaging portion is prepared from 2,4-tolylene diisocyanate, 2,6-tolylene diisocyanate, 3,3'-tolidene 4,4-diisocyanate, diphenylmethane 4,4'-diisocyanate or mixtres thereof.

* * * * *